United States Patent
Barreto

(10) Patent No.: US 11,554,225 B1
(45) Date of Patent: Jan. 17, 2023

(54) HEATING ELEMENT ASSEMBLY FOR VAPORIZER

(71) Applicant: Scope and Stack LLC, Cove, OR (US)

(72) Inventor: Adam Barreto, Cove, OR (US)

(73) Assignee: Scope and Stack LLC, Seattle, WA (US)

( * ) Notice: Subject to any disclaimer, the term of this patent is extended or adjusted under 35 U.S.C. 154(b) by 319 days.

(21) Appl. No.: 16/882,303

(22) Filed: May 22, 2020

Related U.S. Application Data

(60) Provisional application No. 62/852,166, filed on May 23, 2019.

(51) Int. Cl.
*A61M 11/04* (2006.01)

(52) U.S. Cl.
CPC ... *A61M 11/042* (2014.02); *A61M 2205/0211* (2013.01); *A61M 2205/0288* (2013.01); *A61M 2205/3653* (2013.01); *A61M 2205/8206* (2013.01)

(58) Field of Classification Search
CPC ........ A61M 11/042; A61M 2205/0288; A61M 2205/3653
See application file for complete search history.

(56) References Cited

U.S. PATENT DOCUMENTS

| | | | | |
|---|---|---|---|---|
| 3,226,528 A | * | 12/1965 | Martin | A47J 31/053 236/94 |
| 3,432,641 A | * | 3/1969 | Welke | A47J 36/2433 219/415 |
| 3,549,861 A | * | 12/1970 | Trachtenberg | A47J 41/005 219/202 |
| 4,049,949 A | * | 9/1977 | Fitzsimons | H05B 3/00 206/315.9 |
| 6,894,457 B2 | * | 5/2005 | Germagian | H02M 7/003 363/146 |
| 8,781,306 B2 | * | 7/2014 | Hatten | A61M 16/1075 392/386 |
| 10,085,481 B2 | * | 10/2018 | Verleur | A24F 40/40 |
| 2011/0308521 A1 | * | 12/2011 | Kofford | A61M 11/041 128/203.27 |
| 2017/0231283 A1 | | 8/2017 | Gadas | |
| 2018/0043115 A1 | | 2/2018 | Gould et al. | |
| 2018/0199627 A1 | * | 7/2018 | Bowen | A24D 3/17 |
| 2018/0304032 A9 | | 10/2018 | Trzecieski | |

* cited by examiner

*Primary Examiner* — Neil Abrams
(74) *Attorney, Agent, or Firm* — Klarquist Sparkman, LLP

(57) ABSTRACT

A heating element assembly for a vaporizing apparatus can include a housing, a heating element disposed within the housing, a magnetic connector, and a spacing member. The housing can comprise an outer wall defining an inner bore and a base portion disposed within the inner bore, the base portion defining an upper well portion and a lower well portion. The upper well portion can receive at least a portion of a therapeutic agent container. The heating element can increase in temperature when a current is applied. The magnetic connector can be disposed at least partially within the housing and coupled to the heating element. The spacing member can be disposed between the heating element and the magnetic connector. The magnetic connector can be configured to couple an electric power source.

18 Claims, 21 Drawing Sheets

FIG. 20

HEATING ELEMENT ASSEMBLY FOR VAPORIZER

CROSS-REFERENCE TO RELATED APPLICATION

This application claims the benefit of U.S Provisional Application Ser. No. 62/852,166, entitled HEATING ELEMENT ASSEMBLY FOR VAPORIZER, filed on May 23, 2019, which is incorporated by reference herein in its entirety.

FIELD

The present disclosure relates generally to systems for volatizing therapeutic agents, such as by heating or vaporizing, and more particularly to heating element assemblies for such systems.

BACKGROUND

Liquids containing therapeutic agents can be vaporized and inhaled for medicinal purposes. Certain therapeutic agents can be prepared for consumption in an oil medium. In order to vaporize therapeutic agent-containing oil, it is typically heated to a high temperature (e.g., between 450° F. –600° F., depending on the particular oil or agent). After agent-containing medium is vaporized, the vapors can be inhaled either directly or after passing the vapor through water.

Vaporizers for use with therapeutic agent-containing oils typically have a container that can be heated to vaporize oil placed within the container. The container is typically a glass structure with an opening at the top that oil can be placed in and a lower surface that can be heated. Some vaporizers have containers that are heated directly with a flame from a blow torch or other device. However, this requires the presence of an open flame, which can be dangerous, and which can make achieving a precise temperature difficult. Alternatively, electronic vaporizers can be used to more precisely heat a container to a particular temperature. Electronic vaporizers typically comprise metal coils that wrap around a container and can be heated by applying a voltage to the coils and running a current through them. This can allow a container to be heated to a precise temperature. However, this requires a high voltage to be applied to the coils, which typically means the vaporizer must be plugged into an electrical outlet in order to provide enough electrical power. Furthermore, because the coils wrap around the container, disturbance of the cables connected to the coils can knock the system over, potentially damaging the entire system and/or presenting a fire hazard.

SUMMARY

Disclosed herein are heating element assemblies for vaporizers for consuming therapeutic agents. In a representative embodiment, a heating element assembly for a vaporizing apparatus comprises a housing comprising an outer wall defining an inner bore and a base portion disposed within the inner bore, the base portion defining an upper well portion and a lower well portion, the upper well portion configured to receive at least a portion of a therapeutic agent container, and a heating element disposed within the housing and configured to increase in temperature when a current is applied to the heating element. The assembly can further comprise a magnetic connector disposed adjacent the housing and configured to be coupled to the heating element, and a spacing member disposed between the heating element and the magnetic connector. The magnetic connector is configured to be coupled to an electric power source.

In some embodiments, the housing can comprise a channel extending through a thickness of the outer wall such that an inner diameter of the housing is variable to clamp the therapeutic agent container, heating element, magnetic connector, and spacing member together. In some such embodiments, the assembly can further comprises a fastener extending across a width of the channel, the fastener configured to retain the housing in a clamped configuration. In some such embodiments, the assembly can further comprise an outer sleeve configured slide over the housing to reduce the inner diameter of the housing.

In some embodiments, the magnetic connector can be disposed at least partially within a magnet holder coupled to the housing. In some such embodiments, the lower well portion can be configured to receive at least a portion of the magnet holder.

In some embodiments, the spacing member can comprise a silicone washer.

In some embodiment, the base portion of the housing can comprise at least a first opening and the spacing member comprises at least a second opening axially aligned with the first opening. In some such embodiments, the heating element can comprise a circular disc and at least one input pin extending from the disc through the first opening of the housing and the second opening of the spacing member. In some such embodiments, the magnetic connector can comprise a main body and at least one output pin extending from the main body through the first opening and the second opening.

In another representative embodiment, a system can comprise a power source configured to output an adjustable current through a cable connected to the power source, a heating assembly couplable to the power source by the cable, a container member coupled to the heating assembly, and a conduit assembly coupled to and in fluid communication with the container member. The heating assembly comprises a magnetic connector magnetically couplable to the cable and a heating element coupled to the magnetic connector.

In some embodiments, the power source can be a rechargeable battery.

In some embodiments, one end of the cable can have a metallic surface configured to magnetically couple to the magnetic connector.

In some embodiments, the heating assembly can further comprise a housing in which the heating element, a portion of the magnetic connector, and a portion of the container member are disposed, the housing having a diameter variable between a first diameter and a second diameter, the second diameter configured to secure the magnetic connector and the container member against movement relative to the housing. In some such embodiments, the system can further comprise an outer sleeve configured slide over the housing to move the housing from the first diameter to the second diameter. In some such embodiments, the system can further comprise an outer wall having a channel extending through a thickness of the outer wall, and wherein the housing can be secured at the second diameter by a fastener extending across a width of the channel.

In some embodiments, the heating assembly can further comprise a silicone washer positioned between the heating element and the magnetic connector.

In some embodiments, the container member can be configured to be heated by the heating element.

The foregoing and other objects, features, and advantages of the disclosed technology will become more apparent from the following detailed description, which proceeds with reference to the accompanying figures.

BRIEF DESCRIPTION OF THE DRAWINGS

FIG. 20 shows a cross-sectional view of a portion of the system of FIG. 1.

DETAILED DESCRIPTION

Disclosed herein are embodiments of a therapeutic agent delivery or dosing system configured as a vaporizer system that can be used to vaporize liquids, such as medicinal liquids. Such medicinal liquids can include oils, such as oils containing cannabidiol (CBD) or other therapeutic compounds or flavors that can be administered by inhaling the liquid vapors. As described herein, the vaporizer 100 has a portable power source pack (e.g., a battery) and a magnetic housing for a heating element. In certain embodiments, the heating element can be a ceramic heating element, a metallic coil, or other electrical resistance or inductive heating element. The heating element configurations described herein can output a lower voltage than is typically required for traditional electric vaporizers, which can allow for the use of the portable battery pack instead of an electrical outlet. The magnetic housing can allow the power cable to be easily connected or disconnected.

Figure 1:
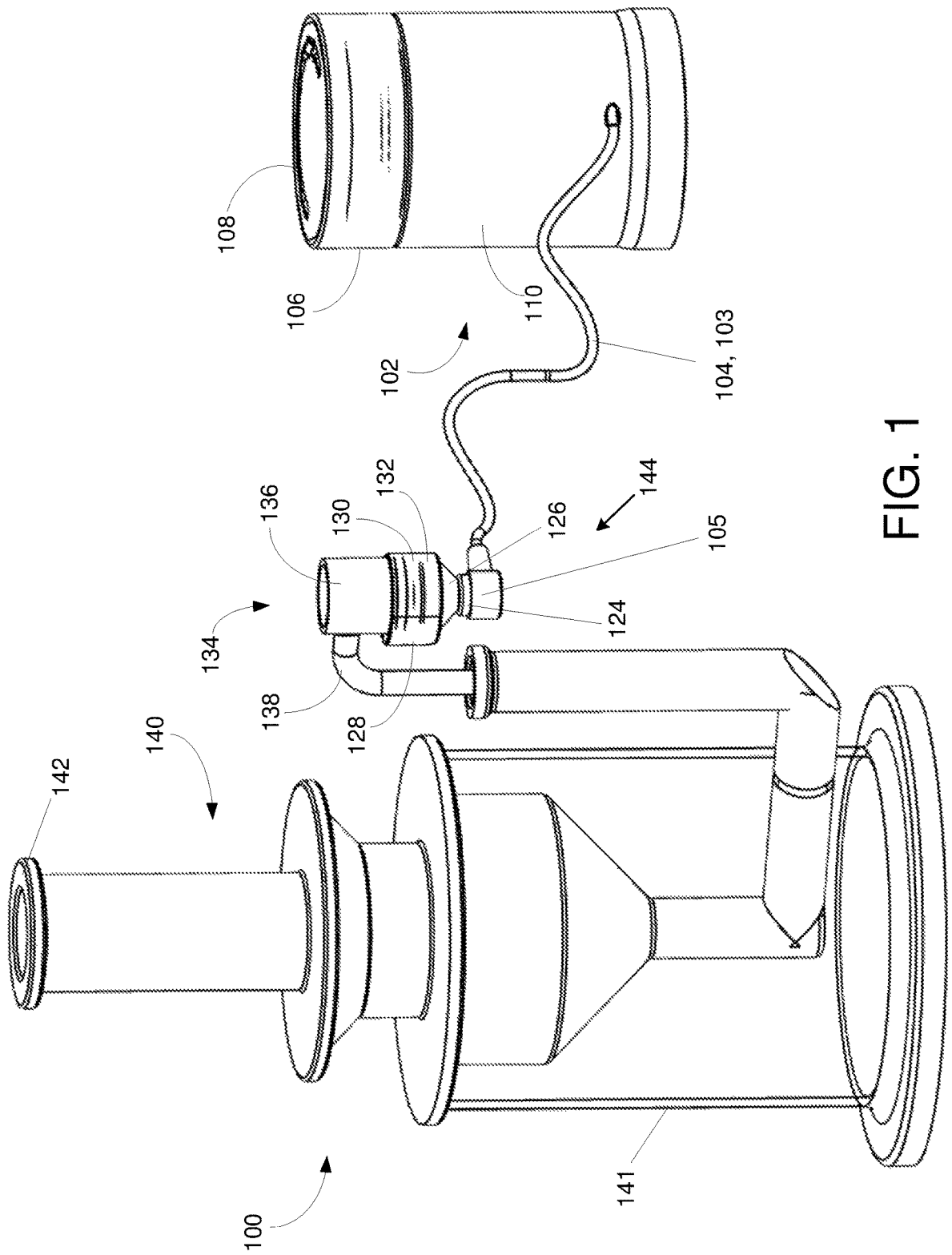
FIG. 1 shows a vaporizer system according to one embodiment.

FIG. 1 shows a vaporizer system 100 according to one embodiment. The vaporizer system 100 can generally comprise a power source 102, a power cable 104, and a heating assembly 144 coupled to the power source via the power cable 104 and comprising a container member or reservoir (e.g., a banger) 134. The system can further comprise a conduit assembly 140 (e.g., configured as an internal recycler, an incycler, or recycler) coupled to the container member 134 and configured to allow a user to inhale oil vapor generated by heating the container member 134 using the heating assembly 144. The heating assembly 144 can generally comprise the container member 134, a housing 128, and heating element 130.

Figure 2:
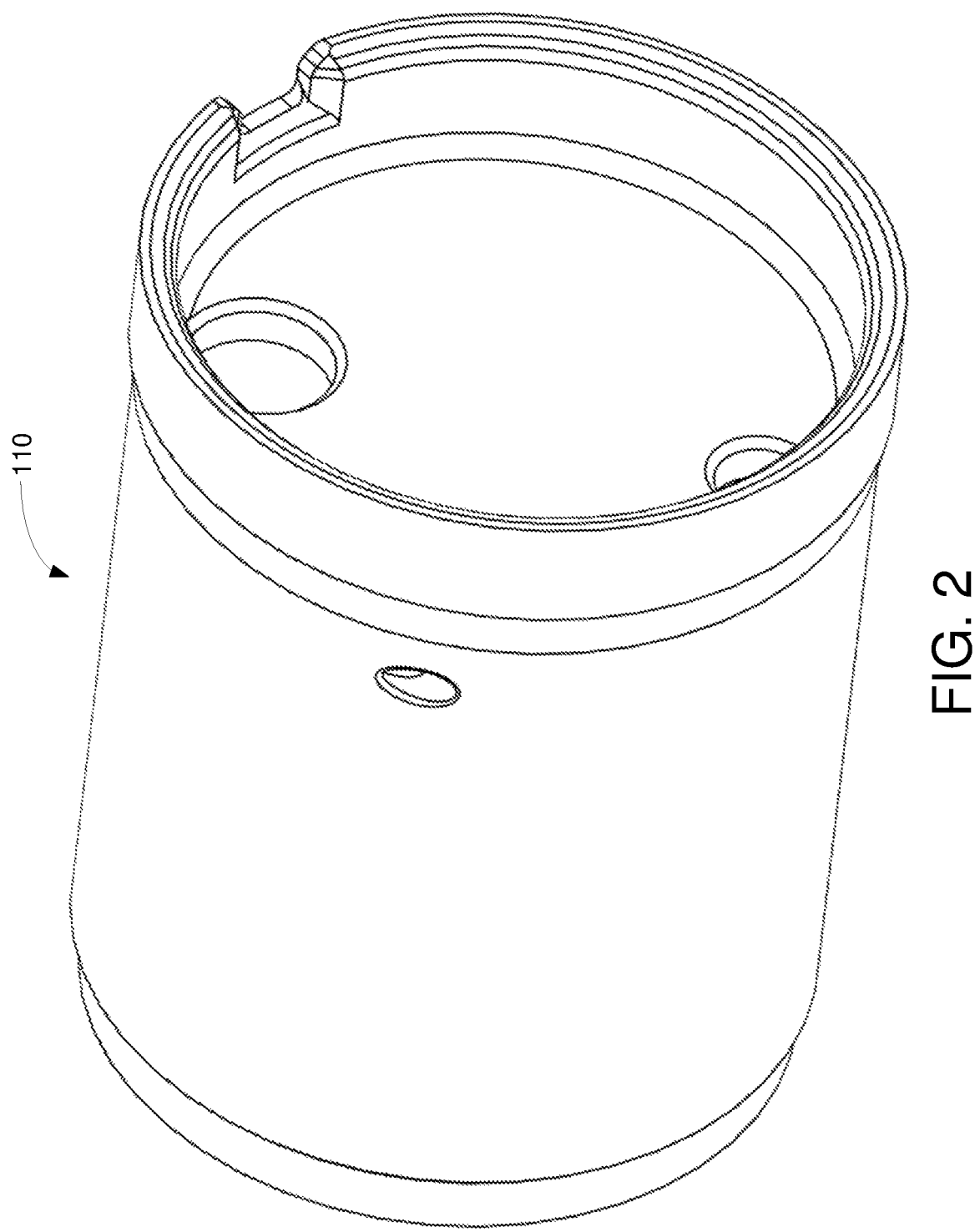
FIG. 2 is a perspective view of an exemplary battery housing of the system of FIG. 1.
Figure 3:
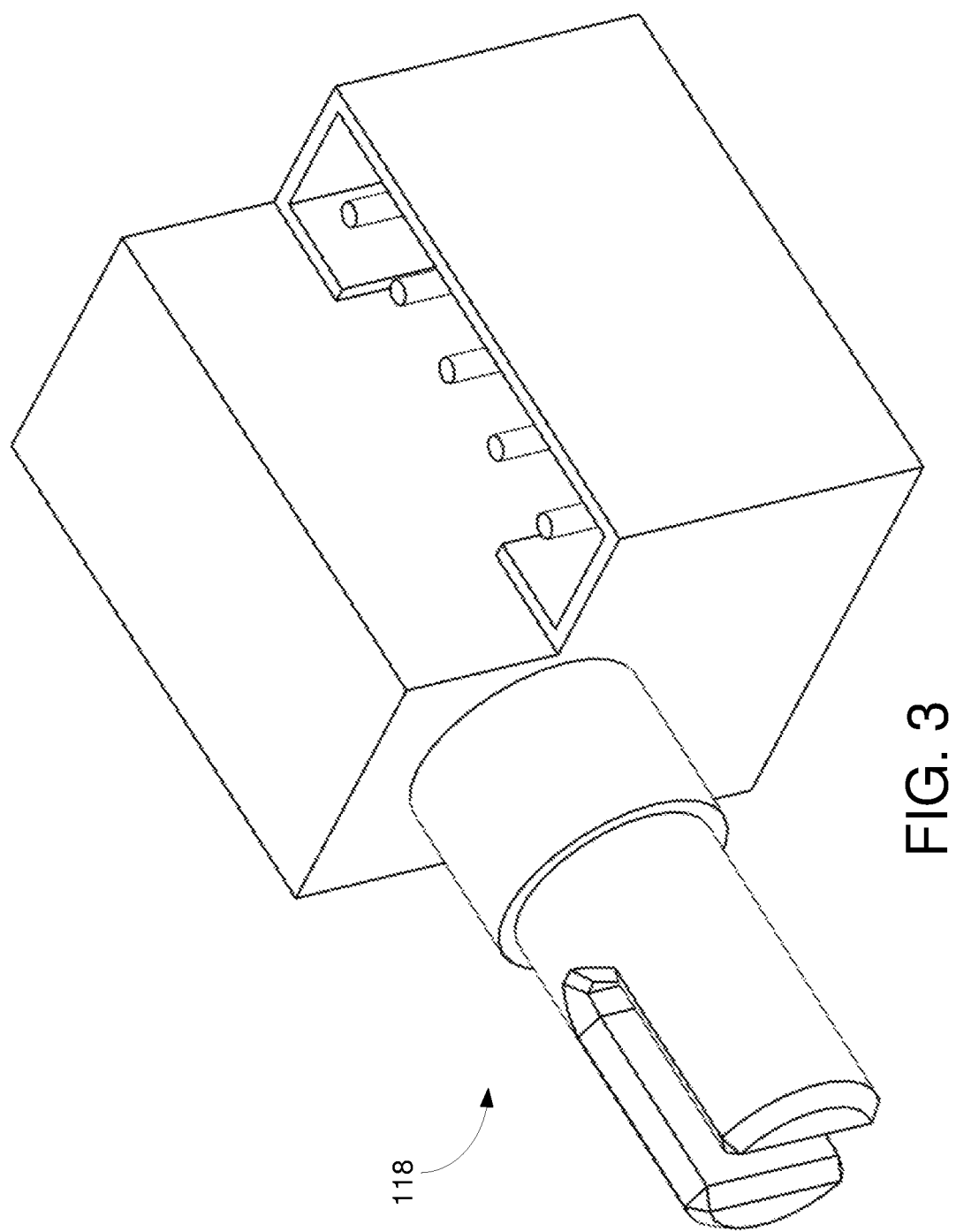
FIG. 3 is a perspective view of an exemplary speed controller of the system of FIG. 1.
Figure 4:
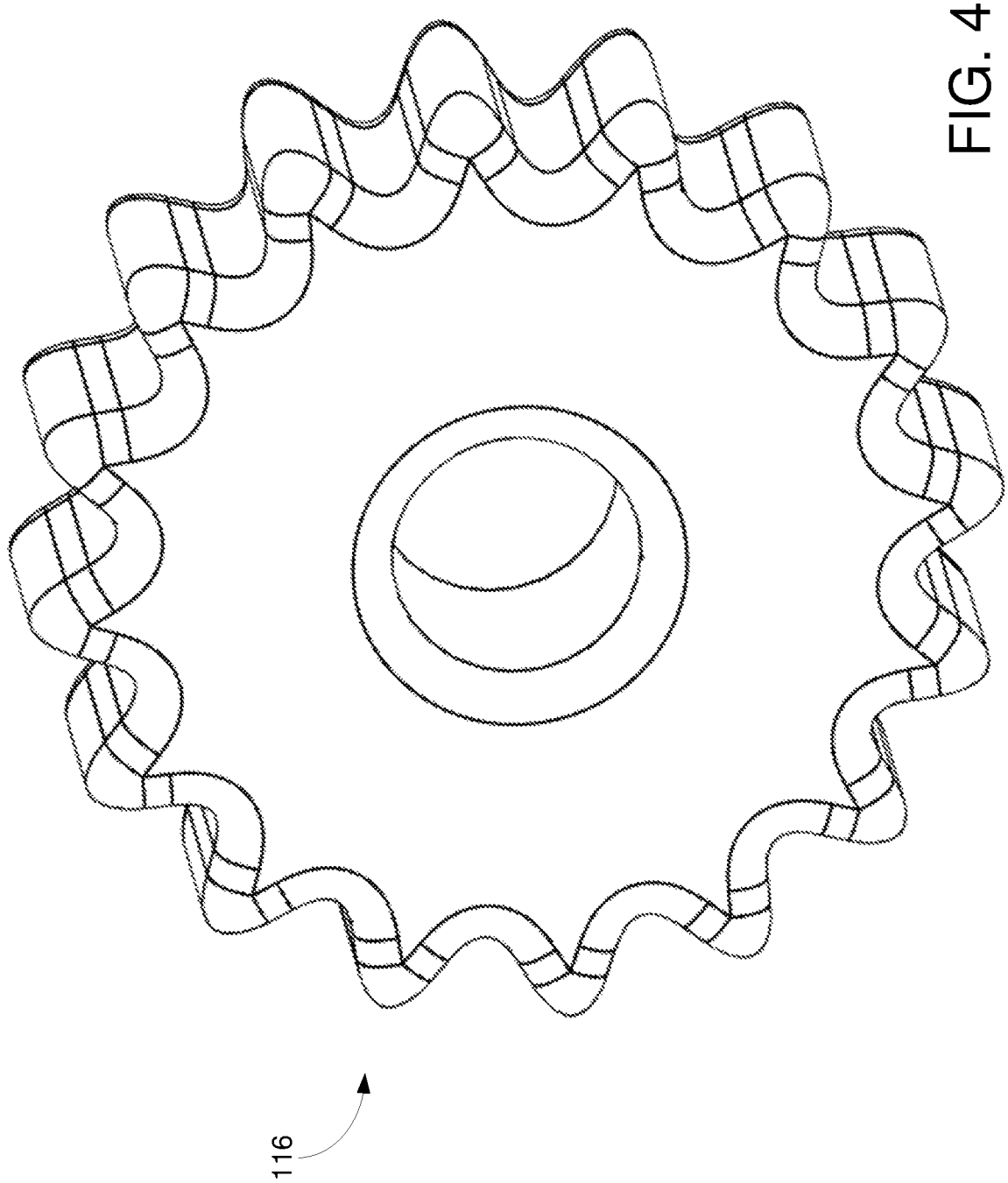
FIG. 4 is a perspective view of an exemplary gear of the system of FIG. 1.
Figure 5B:
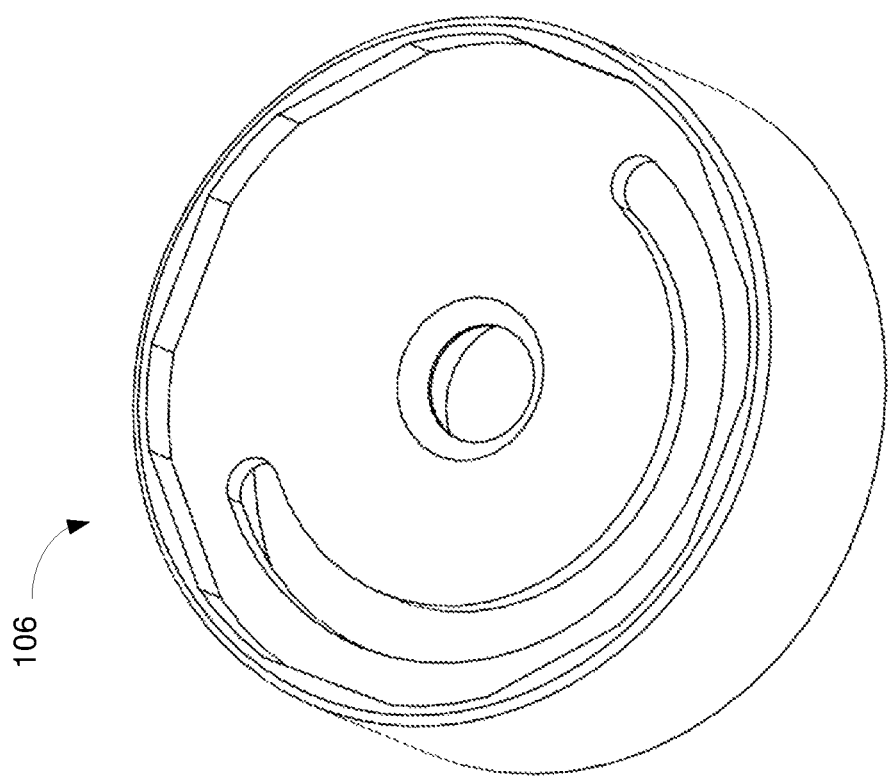
FIGS. 5A and 5B show bottom and top perspective views, respectively, of an exemplary battery gear top of the system of FIG. 1.
Figure 5A:
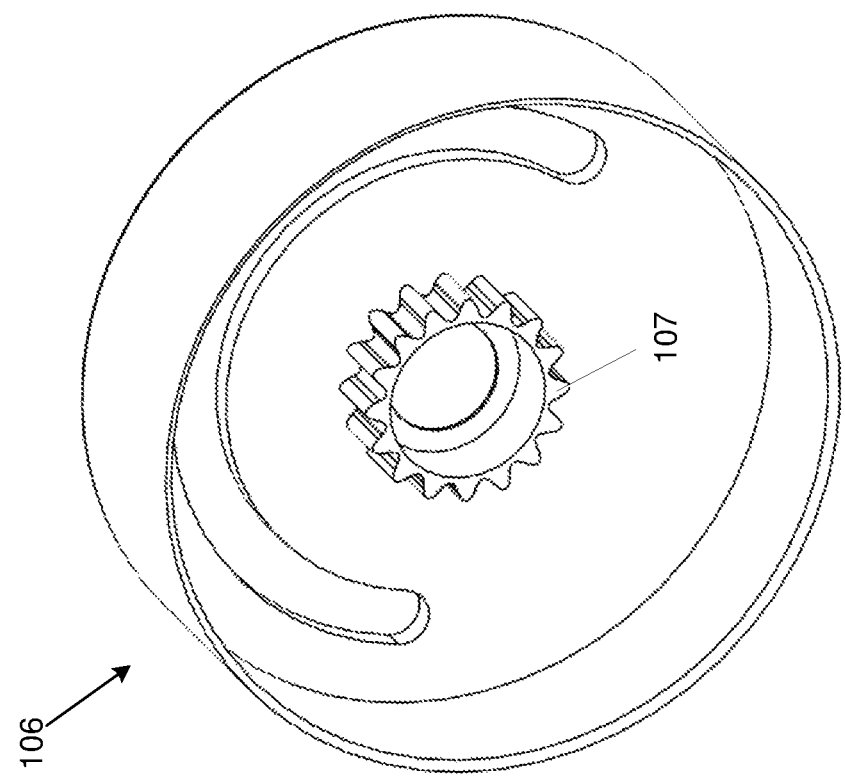
Figure 6:
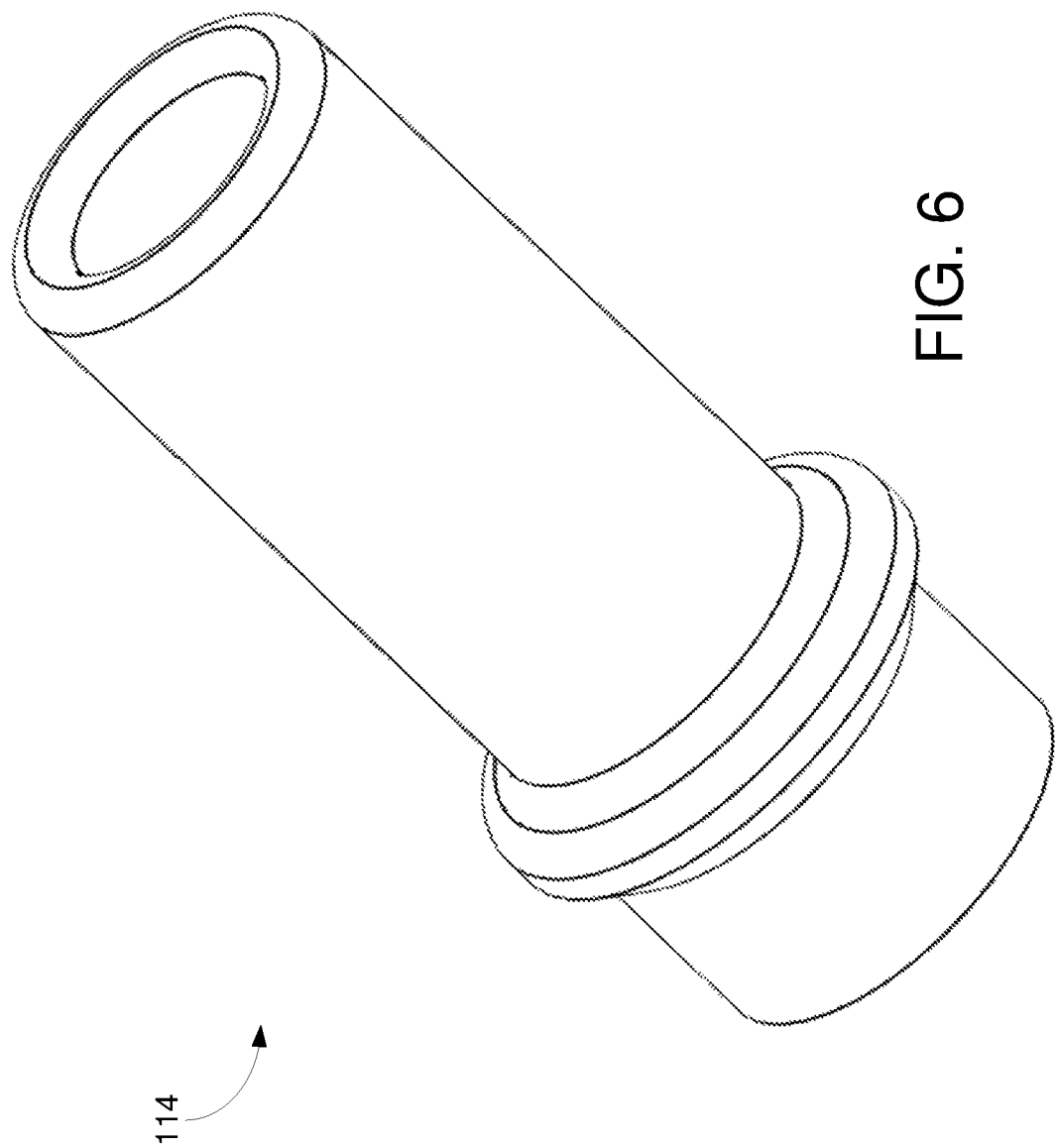
FIG. 6 is a perspective view of an exemplary pin of the system of FIG. 1.
Figure 7:
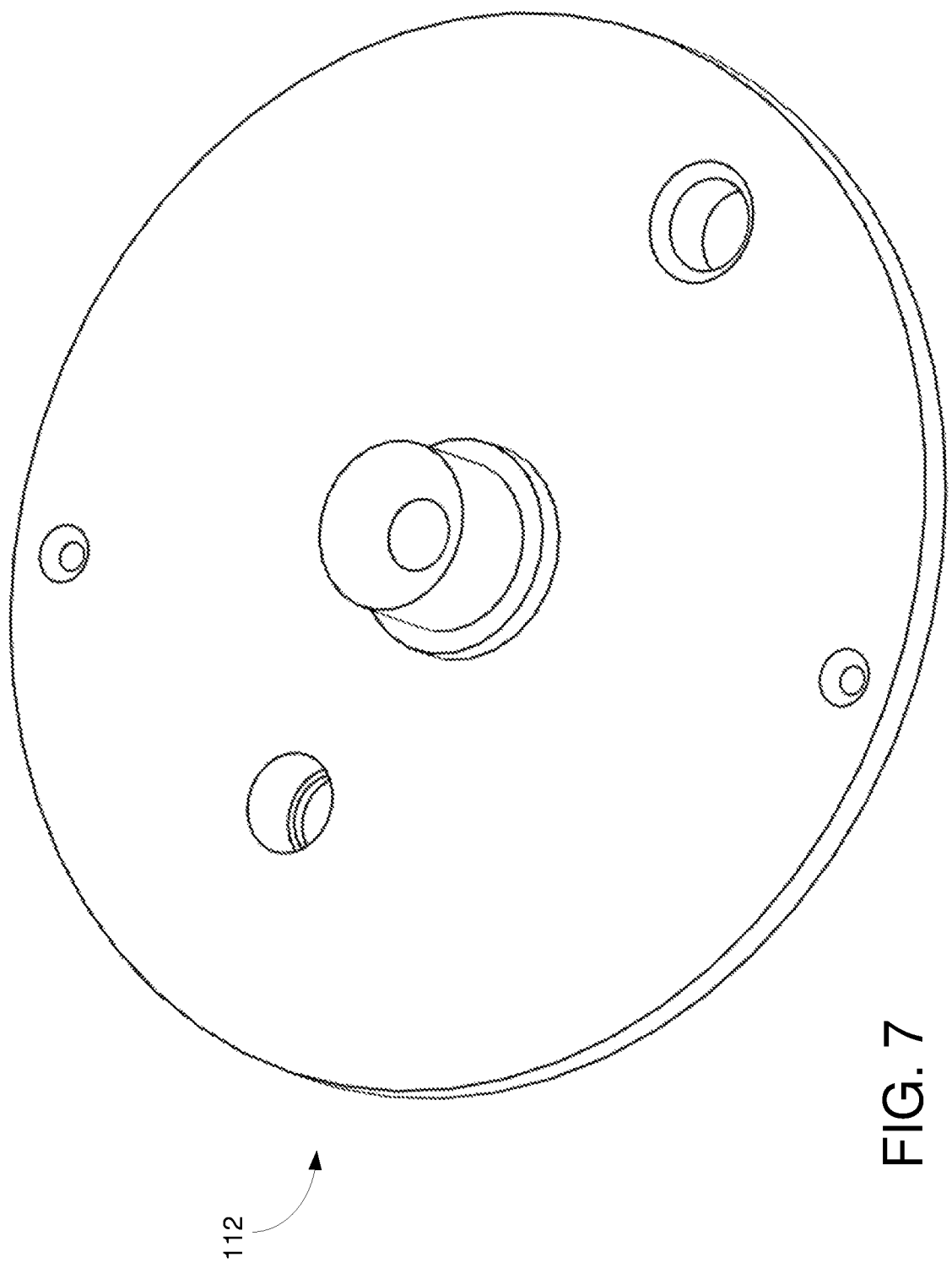
FIG. 7 is a perspective view of an exemplary battery lid of the system of FIG. 1.
Figure 8:
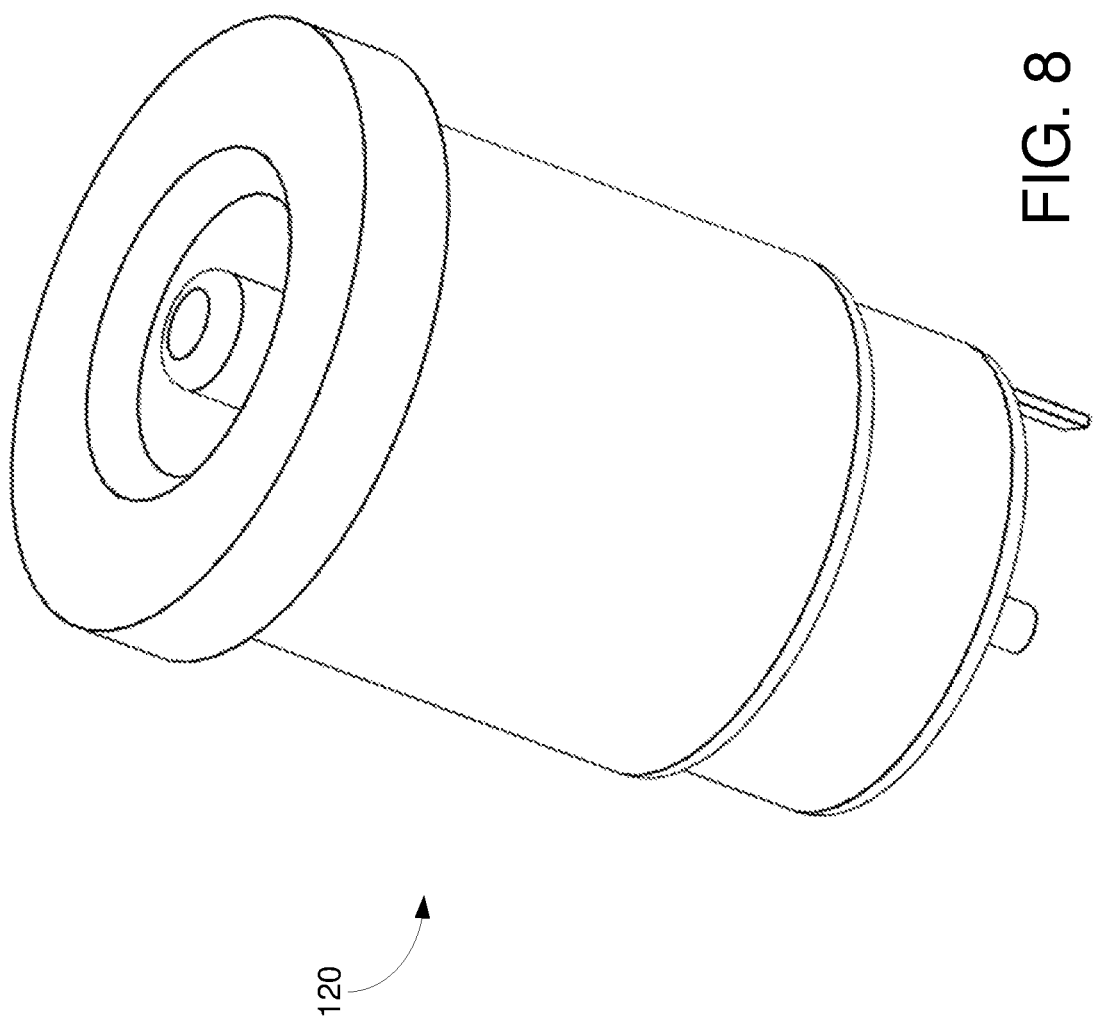
FIG. 8 is a perspective view of an exemplary charging port of the system of FIG. 1.
Figure 9:
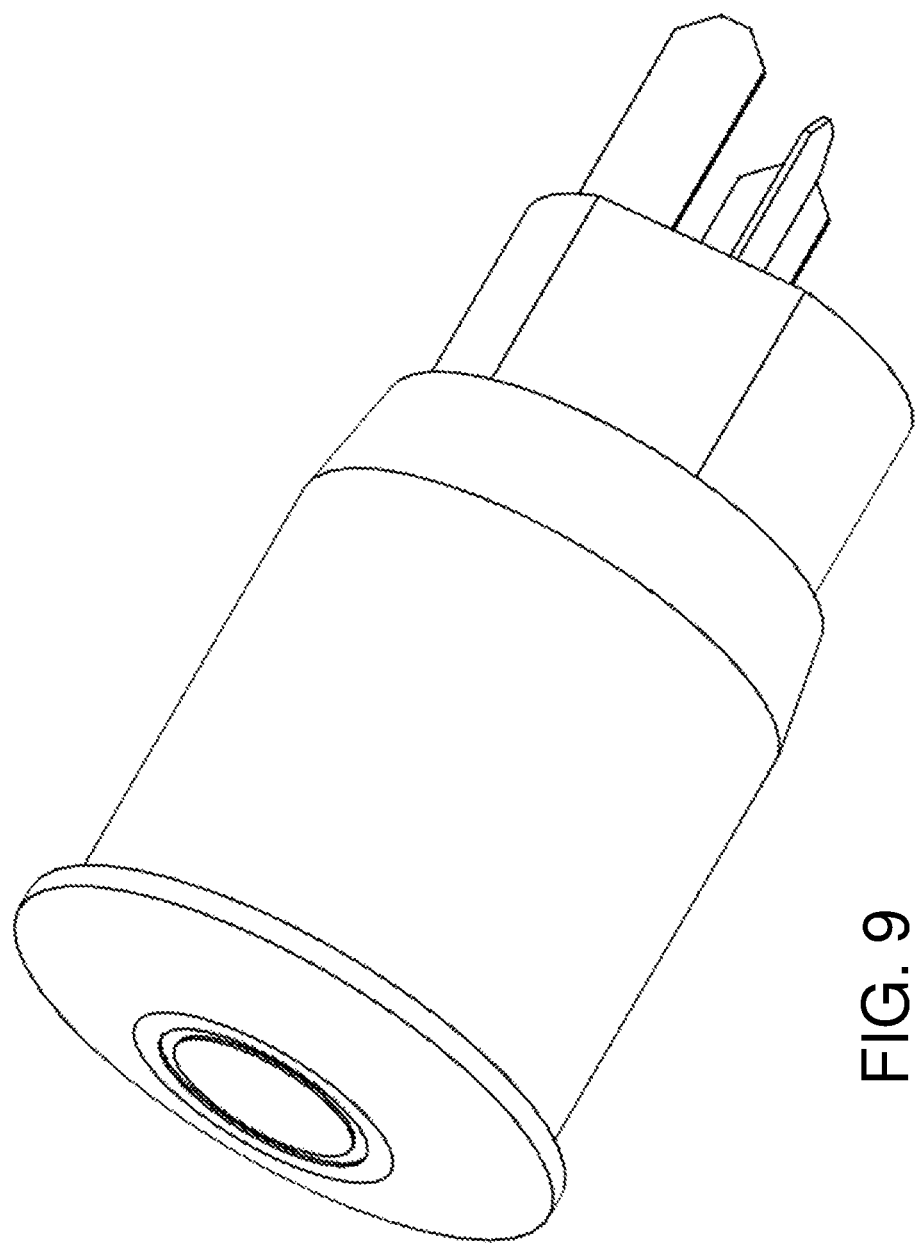
FIG. 9 is a perspective view of an exemplary power switch of the system of FIG. 1.

As mentioned, the vaporizer system 100 comprises a power source 102, such as a battery, connected to a power cable 104. The power source 102 can output a variable voltage/current through the cable 104. In the illustrated embodiment, the power source is a battery 102 that can output a voltage of between 13 V-16 V. In the illustrated embodiment, the battery 102 can have a gear assembly comprising a housing 110 (FIG. 2), a controller 118 (FIG. 3), a gear 116 (FIG. 4), a battery gear top 106 (FIGS. 5A-5B) comprising a gear 107 positioned about a central opening in the top member 106, a pin 114 (FIG. 6), and a lid 112 (FIG. 7). The controller 118 can be, for example, a proportional-integral-derivative (PID) controller, such as a motor or speed controller. In some embodiments, the battery 102 can have a potentiometer that can be used to adjust its voltage/current output. The gear 116 can be attached to the lid 112 and the potentiometer. The gears 107 and 116 can be meshed together such that rotating the outer gear top member 106 of the battery 102 rotates the gear 116, which can turn the lid 112 and adjust the potentiometer to change the voltage/current output by the battery 102. The battery 102 can also comprise a charging port 120 (FIG. 8) for recharging the battery and a power switch 122 (FIG. 9). The battery 102 can be connected to a wall outlet to charge (e.g., via charging portion 120) and then can be disconnected such that it is portable and still able to operate. In other embodiments, the battery (or other power source) can be coupled to an alternative means of charging such as, for example, a solar panel. In still other embodiments, the battery can be replaceable rather than rechargeable.

Figure 10B:
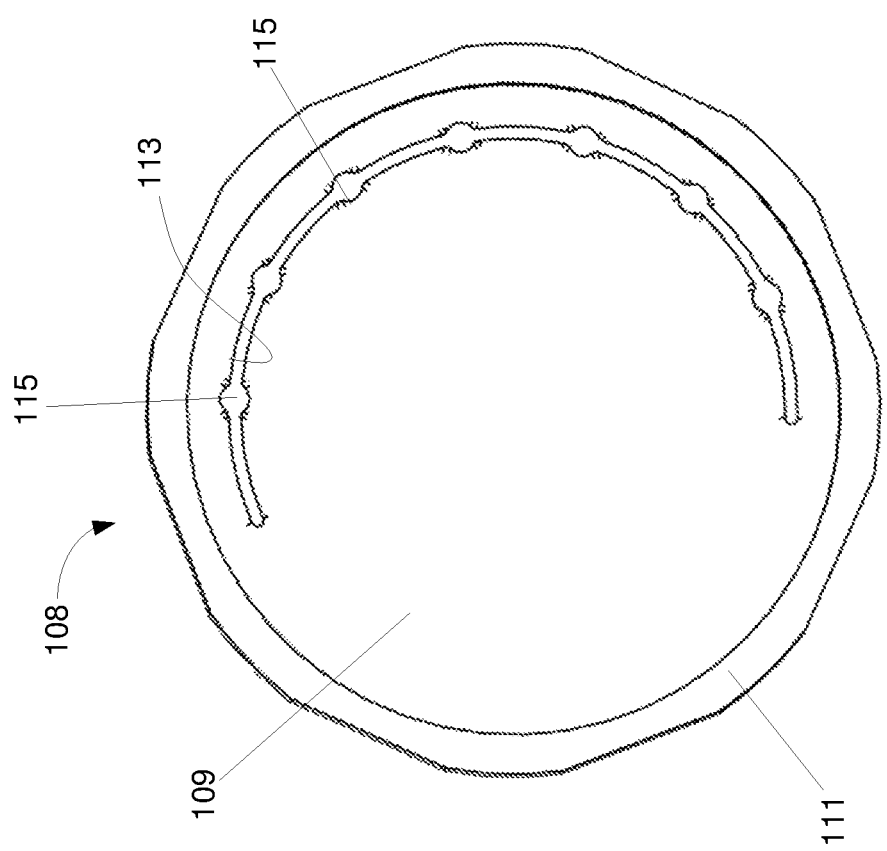
FIGS. 10A and 10B show top and bottom plan views, respectively, of an exemplary cap of the system of FIG. 1.
Figure 10A:
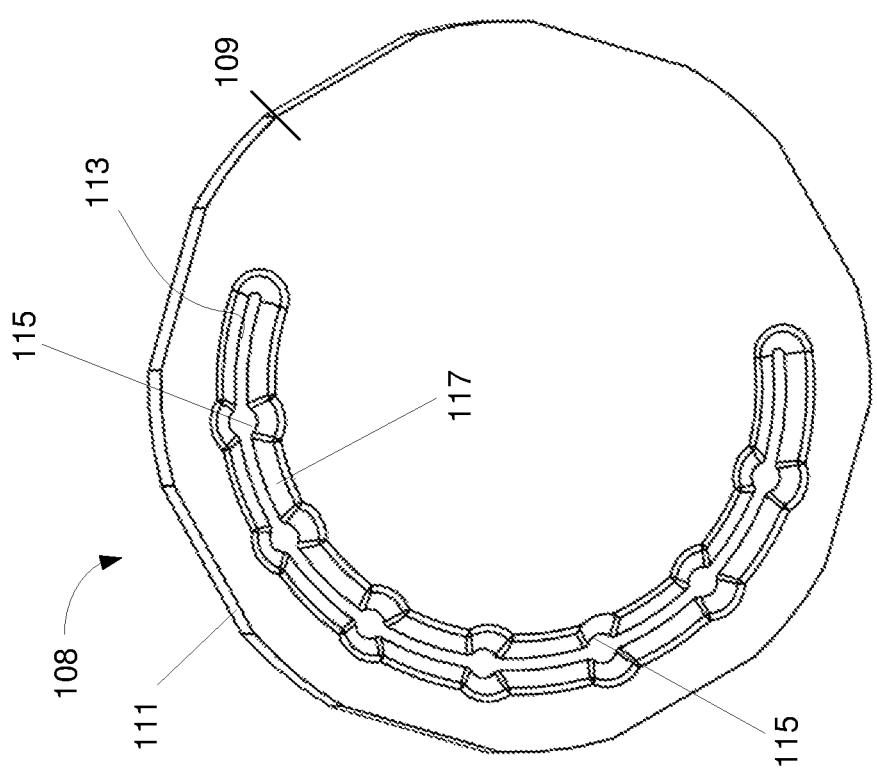

In some embodiments, the system 100 can further comprise a power source cap 108, as shown in FIGS. 10A-10B. The power source cap 108 can include a lid member 109, an outer wall 111, and a crescent-shaped opening 113 extending through a thickness of the lid member 109. In the illustrated embodiment, the opening 113 can comprise an elongated slot including a plurality of circular openings 115. The opening 113 can be disposed in a recess 117 disposed on a outer surface of the lid member 109.

Figure 11:
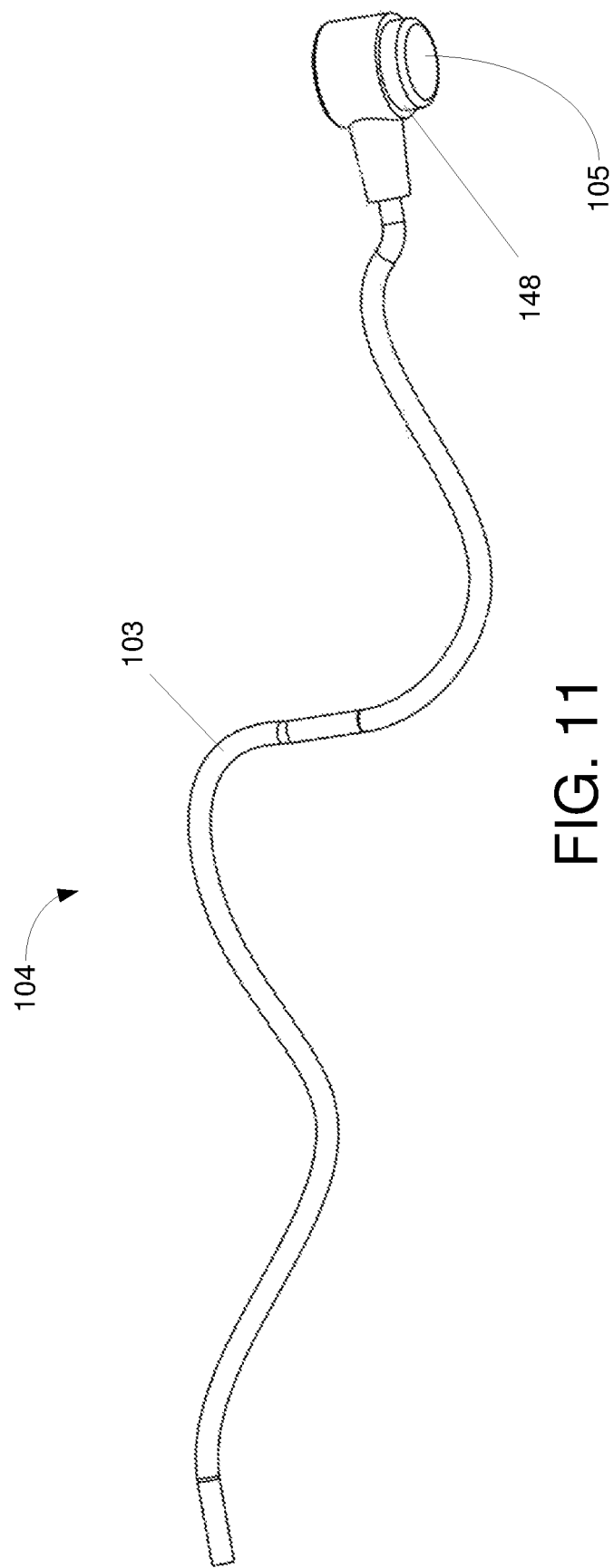
FIG. 11 is a perspective view of an exemplary power cable of the system of FIG. 1.
Figure 12:
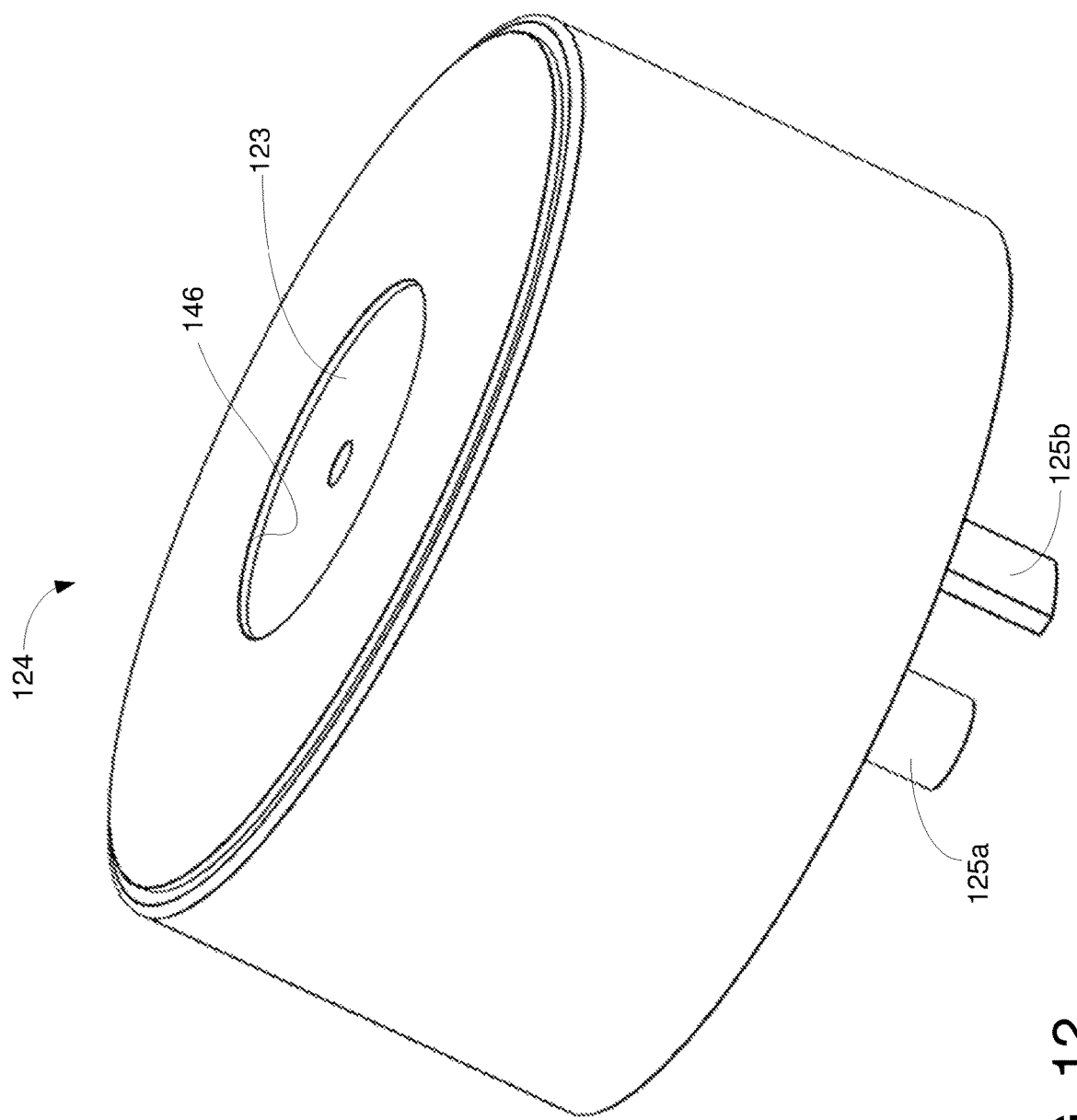
FIG. 12 is a perspective view of an exemplary magnetic connector of the system of FIG. 1.

Referring to FIG. 11, the power cable 104 can comprise a cable body 103 and metallic and/or magnetic connector 105. The power cable 104 can be configured to couple the power source 102 to the heating assembly 144, using the magnetic connector 105. As the battery 102 outputs a voltage/current, because the connector 105 is connected to the cable body 103, the connector 105 comprises the voltage/current output by the battery 102. As shown in FIG. 1, the metallic connector 105 can be magnetically coupled to a magnetic connector 124 of the heating assembly 144. Referring to FIG. 12, the magnetic connector 124 can comprise a magnetic portion 123. The magnetic portion 123 can be sized and shaped to engage the metallic connector 105 of the power cable 104. For example, in the illustrated embodiment, the magnetic portion 123 can comprise a circular recess 146 sized to fit a circular protrusion 148 (FIG. 11) of the magnetic connector 105. The magnetic portion 123 can comprise a magnet that creates a magnetic field and thereby attracts metallic objects such as the metallic connector 105. The magnetic strength of the magnetic portion 123 can be such that the metallic connector 105 firmly connects to the magnetic connector 124 of the heating assembly 144 when they are engaged with each other but can be easily removed from the magnetic connector 124 without the use of excessive force.

Figure 20:
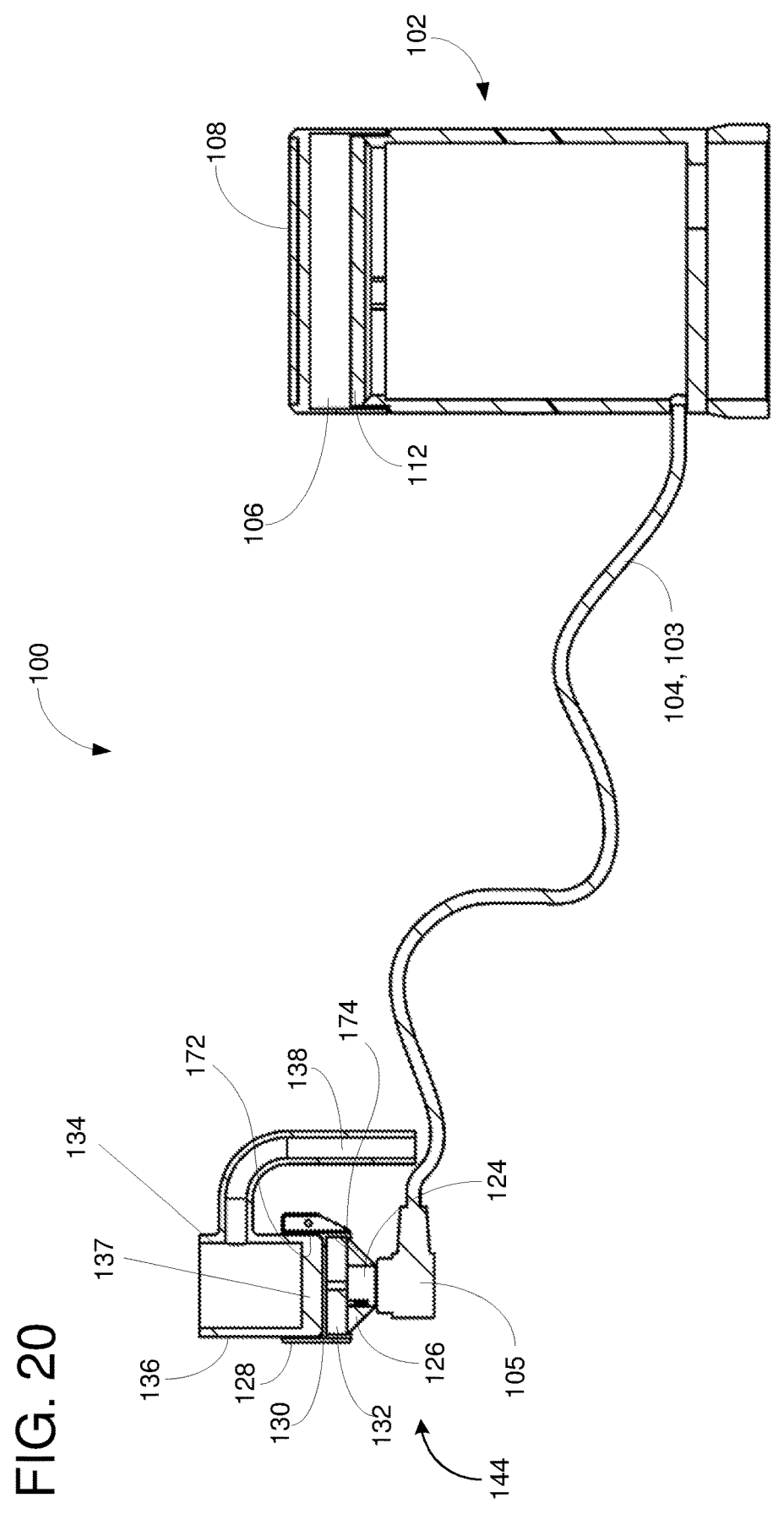

As shown in FIG. 20, the heating assembly 144 can comprise a container member 134, a housing 128 that houses the heating element 130 and positions the heating element 130 adjacent the container member 134, a magnet holder 126 coupled to the housing 128, and the magnetic connector 124, which can be disposed within the magnet holder 126.

Figure 13B:
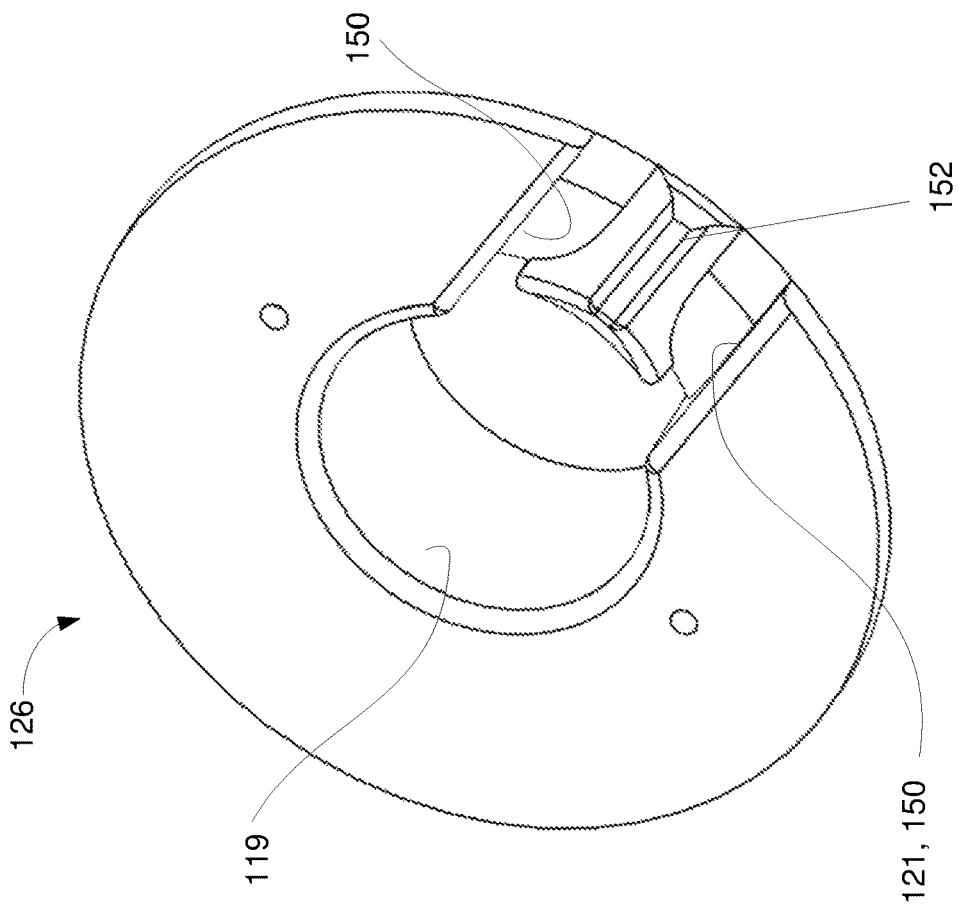
FIGS. 13A and 13B show overhead and underside perspective views, respectively, of an exemplary magnet holder of the system of FIG. 1.
Figure 13A:
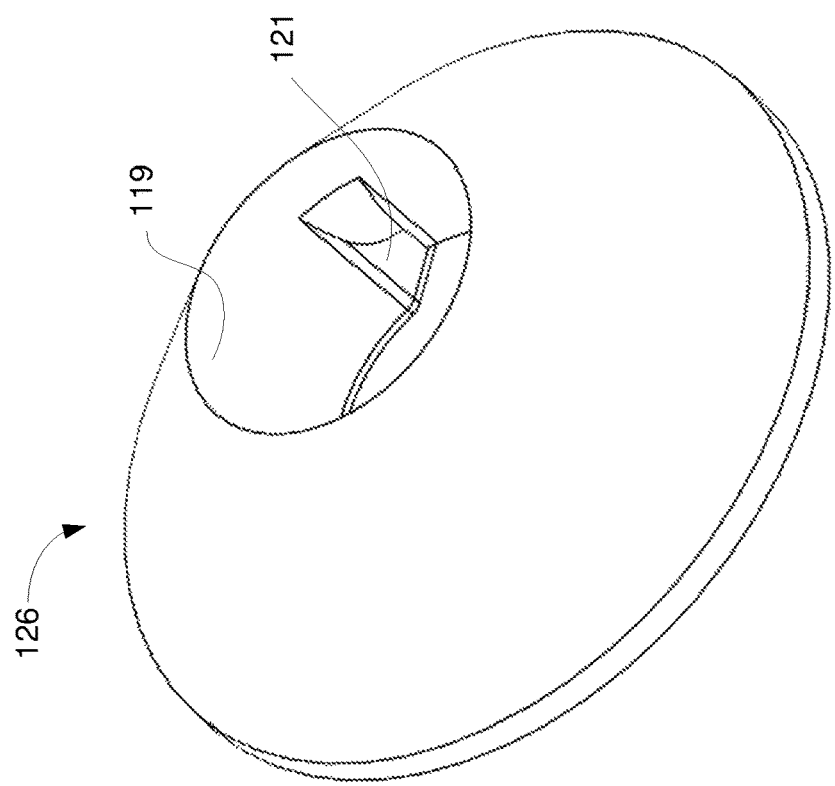

The magnetic connector 124 can be housed in a magnet holder 126, shown in FIGS. 13A-13B. In the illustrated embodiment, the magnet holder 126 has a truncated conical or frustoconical shape including an inner bore 119. In some embodiments, the magnet holder can include one or more cutouts 121. For example, in the illustrated embodiment, the magnet holder includes a cutout 121 extending from the inner bore 119 to an outer surface of the magnet holder 126. In the illustrated embodiment, the cutout 121 comprises two channels 150 separated by a wall portion 152. In the illustrated embodiment, the magnet holder 126 comprises aluminum. In other embodiments, the magnet holder 126 can comprise other materials including polymers such as acrylonitrile butadiene styrene (ABS) plastics, metals such as aluminum, titanium, and/or steel, or any other material(s) strong enough to hold the magnetic connector 124.

When the magnetic connector 124 is coupled to the connector 105, as shown in FIG. 1, the voltage/current output by the battery 102 is applied to the magnetic connector 124. The magnetic connector 124 can have two output pins 125a and 125b (FIG. 12) to apply the received voltage/current to, for example, a heating element 130, as described below. Because the connector 124 is magnetically coupled to the connector 105, jostling of the cable 104 or other components of the vaporizer 100 can cause the connectors 105 and 124 to disconnect rather than toppling the entire system 100 and potentially causing damage to the components. Thus, this magnetic coupling can enhance system safety.

Figure 15:
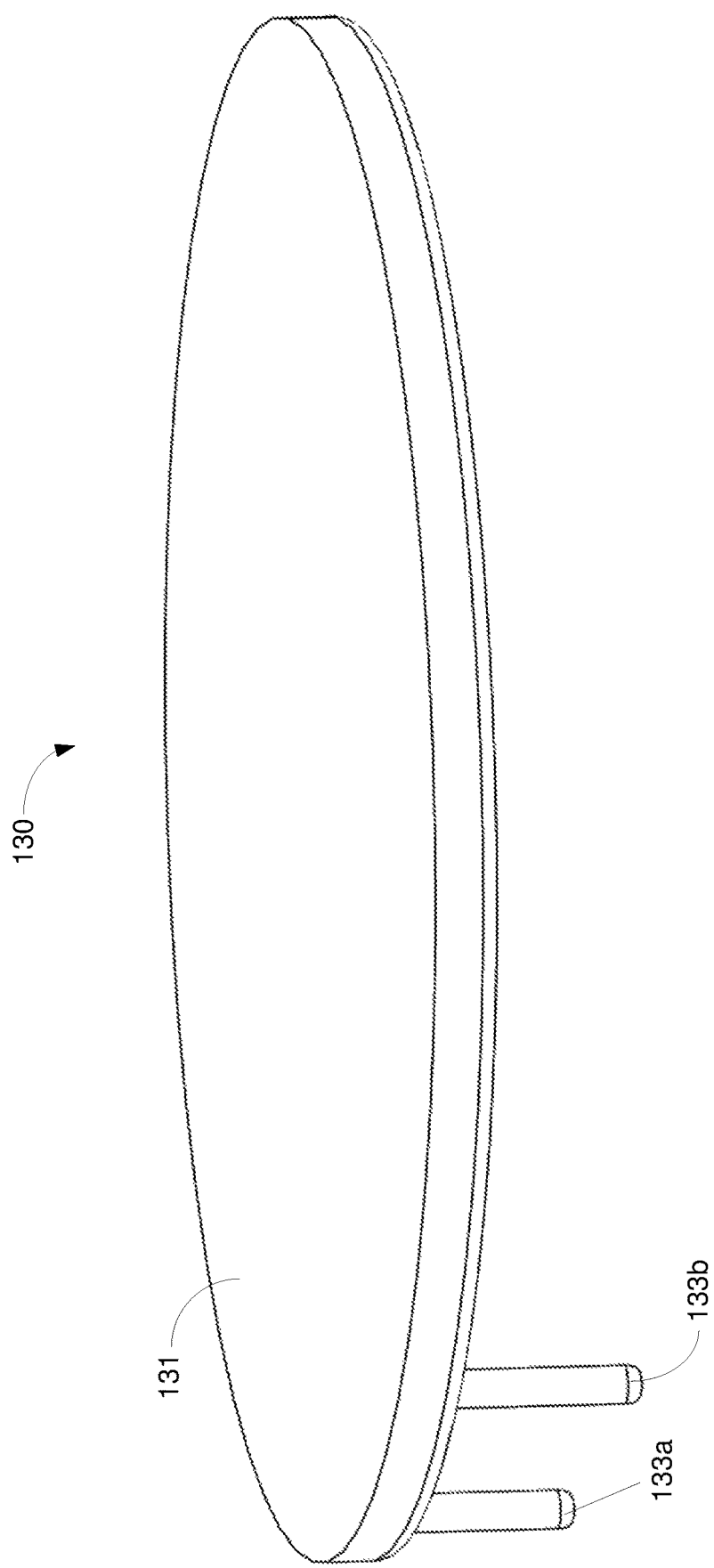
FIG. 15 shows an exemplary heating element of the system of FIG. 1.

In the configuration shown in FIG. 15, the heating element 130 can comprise a ceramic plate 131 and two input pins 133a and 133b. In the illustrated embodiment, the input pins 133a, 133b extend from a surface of the ceramic plate at a substantially 90 degree angle, however, in other embodiments the input pins can be arranged in any orientation. In the illustrated embodiment, the input pins are disposed on a first end portion of the ceramic plate and are located adjacent one another. In other embodiments, the input pins may be disposed in any configuration on the ceramic plate 131. The input pins 133a, 133b of the heating element 130 can be connected to the output pins 125a, 125b of the magnetic connector 124 (FIG. 12). This causes current output by the battery 102 to be applied to the heating element 130 thereby heating the ceramic plate 131. In the illustrated embodiment, the temperature of the heating element 130 can range from 0° F. –1100° F. based on the voltage/current output by the battery 102. In some embodiments, the heating element can range in temperature from 0° F. –800° F.

Figure 14:
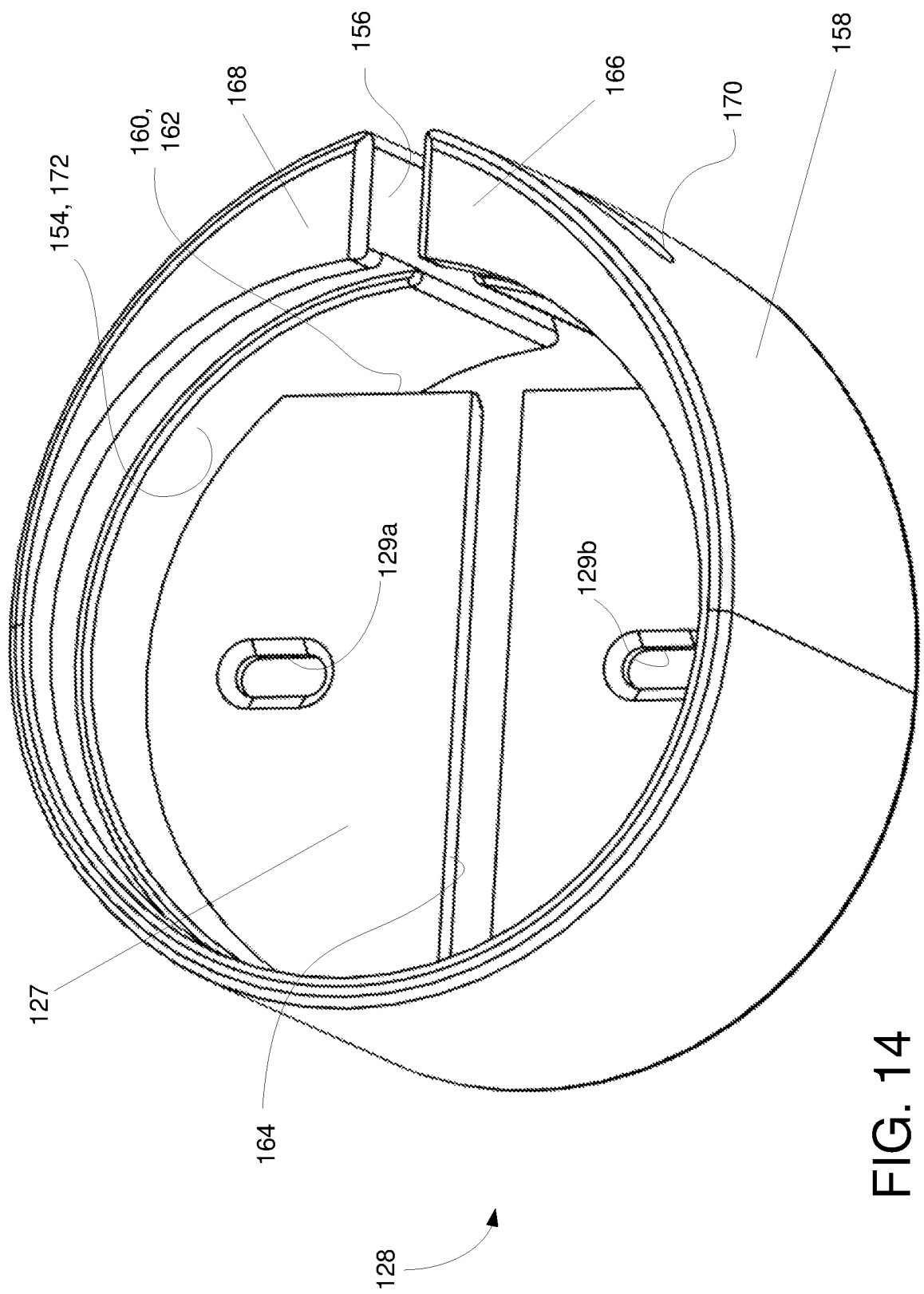
FIG. 14 shows an exemplary holder of the system of FIG. 1.

A holder or housing 128, shown in FIG. 14, can house the heating element 130, position the heating element between the magnetic connector 124 and the container member 134, and couple the heating assembly 144 together. In the illustrated embodiment, the holder 128 is made of aluminum, but can also be made of any suitable heat-resistant material such as any of various metals, quartz, ceramics, glass, etc. The holder 128 can have a base 127 upon which the heating element 130 can rest. The base 127 of the holder 128 can comprise two openings 129a, 129b extending through the base 127 of the holder and through which the output pins 125a, 125b of the magnetic connector 124 and/or the input pins 133a, 133b of the heating element 130 can extend. As shown in the illustrated embodiment, the housing 128 can be an annular member/cylindrical tube/adjustable collar comprising an inner diameter portion or inner bore 154, and the base 127 can be disposed within the inner bore 154 such that a well is defined on either side of the base 127. For example, the housing 128 can comprise an upper well 172 into which a portion of the container member 134 can be disposed and a lower well 174 (FIG. 20) into which a portion of the magnet holder 126 can be disposed.

Figure 21:
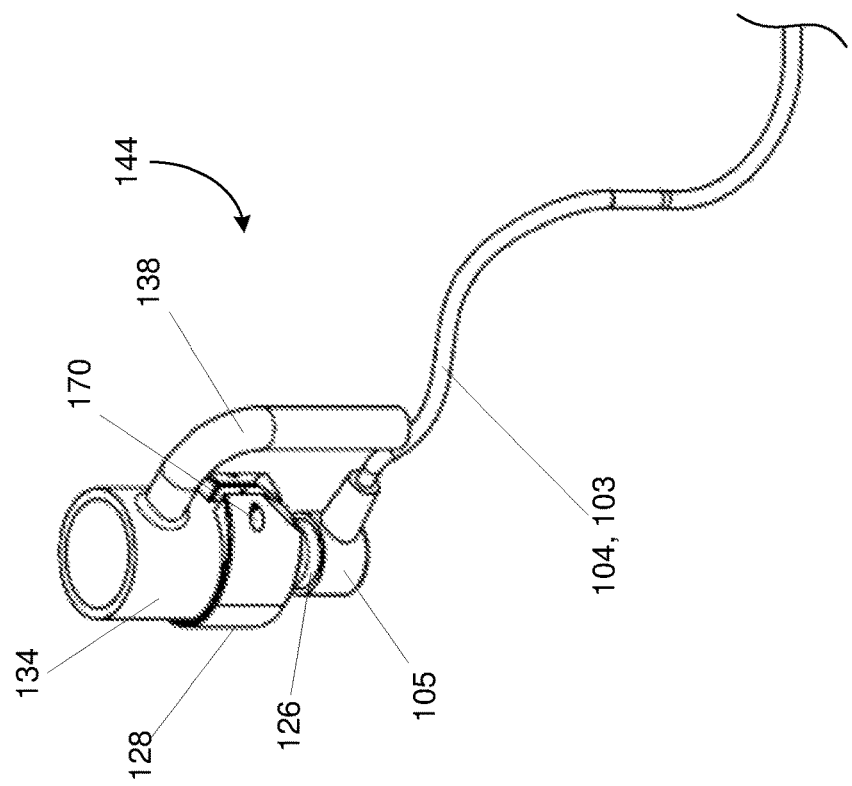
FIG. 21 shows a perspective view of a portion of the system of FIG. 1.

As shown in FIG. 14, the housing 128 can be configured as a clamp member having an opening or channel 156 extending through a thickness of the outer wall 158 of the housing 128, that defines a first portion and a second portion 166, 168 of the outer wall 158. The inner diameter of the housing 128 can be varied by moving the first and second portions 166, 168 nearer and/or further relative to one another. The first and second portions 166, 168 can each comprise an aperture 170. A fastener such as a screw (not shown) can extend through the apertures 170 to couple the first and second portions 166, 168 together and can be used to tighten the housing 128 around one or more other components of the heating assembly 144 (including the container member 134) in order to clamp/engage/retain the components together, as shown in FIG. 21.

In some embodiments, the outer wall 158 can have a non-uniform thickness around the circumference of the housing 128. For example, in the illustrated embodiment, the portion of the outer wall 158 comprising the channel 156 is thicker than the opposite portion of the outer wall 158. However, in other embodiments, the outer wall 158 can have a substantially uniform thickness around the circumference of the housing. As shown in FIG. 14, the lower wall 127 of the housing 128 can further comprise a substantially T-shaped opening 160 including a head portion 162 aligned with the channel 156 in the outer wall 158, and a body portion 162 extending from the head portion to the opposing portion of the outer wall 158. The T-shaped opening 160 can give the housing 128 additional flexibility such that the housing 128 can serve as a clamp.

Figure 16:
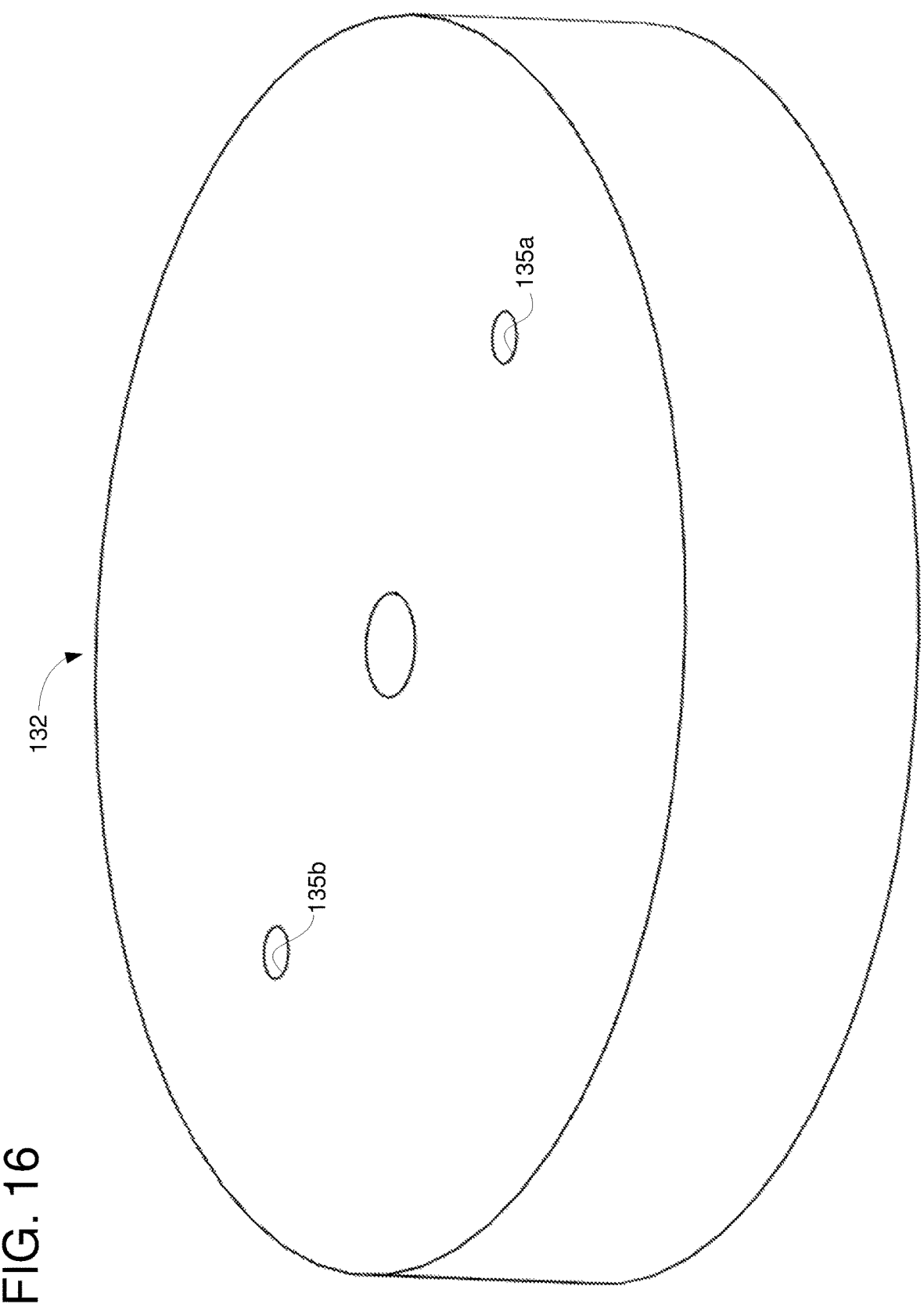
FIG. 16 shows an exemplary silicone washer member of the system of FIG. 1.

In certain embodiments, if the temperature of the magnetic connector 124 rises above a certain threshold (e.g., approximately 130° F.), the magnetic connectivity of the connector 124 with the connector 105 of the cable 104 can be degraded. Thus, a spacing member 132 (FIG. 16), such as a disk or washer, can be positioned between the heating element 130 and the magnetic connector 124 to separate and thermally isolate the heating element 130 from the magnetic connector 124, as shown in FIG. 20. This can prevent the temperature of the connector 124 from significantly increasing as the temperature of the heating element 130 increases during operation of the system 100. The washer 132 can comprise any thermally insulative, heat resistant materials such as silicone or other polymers, glass, fiberglass, (e.g., fiberglass exhaust shielding), etc. In certain embodiments, the washer 132 comprises silicone. The washer 132 can comprise two openings 135a, 135b through which the output pins 125a, 125b of the magnetic connector 124 and/or the input pins 133a, 133b of the heating element 130 can extend.

Figure 17:
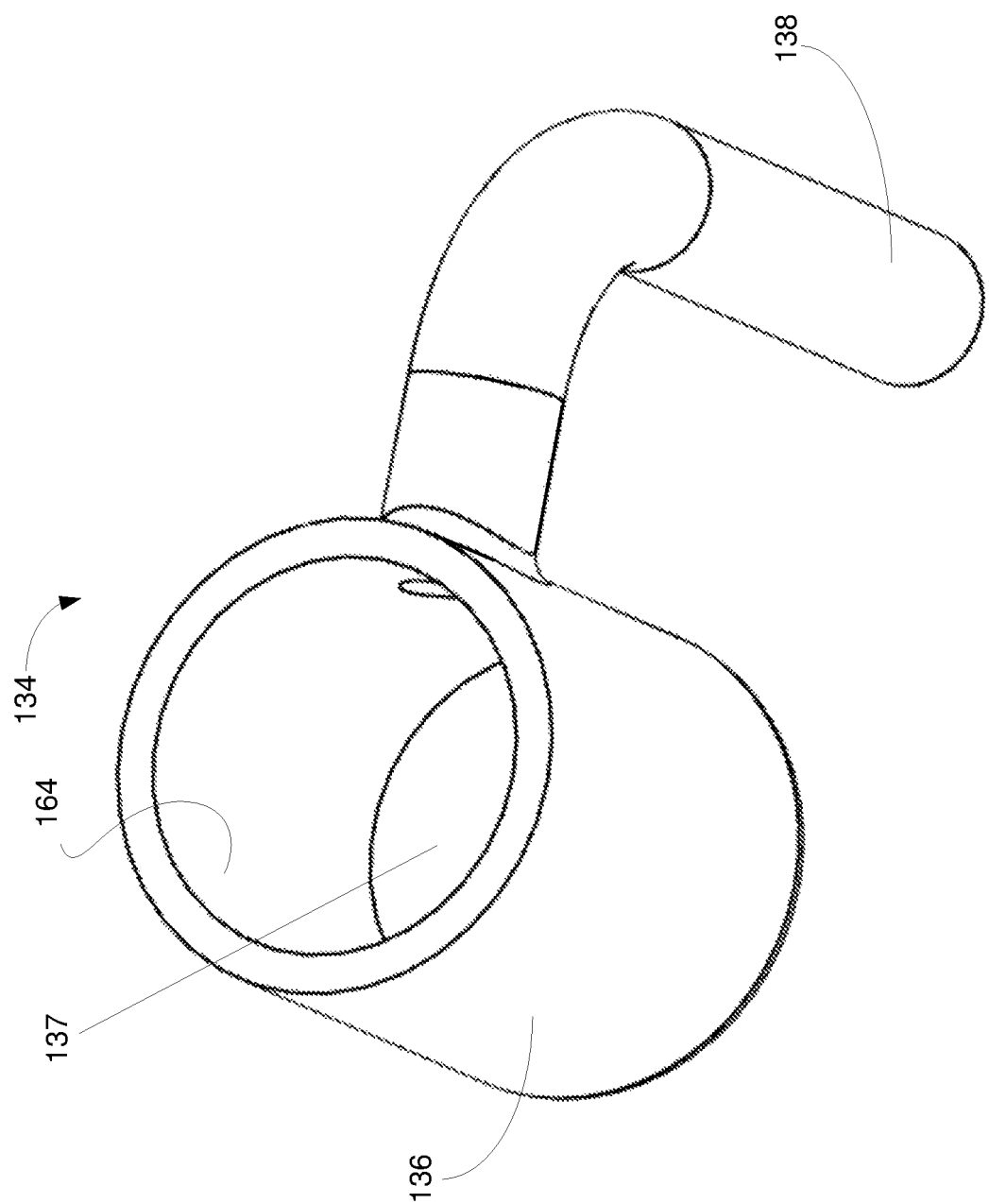
FIG. 17 shows an exemplary container member of the system of the FIG. 1.
Figure 18:
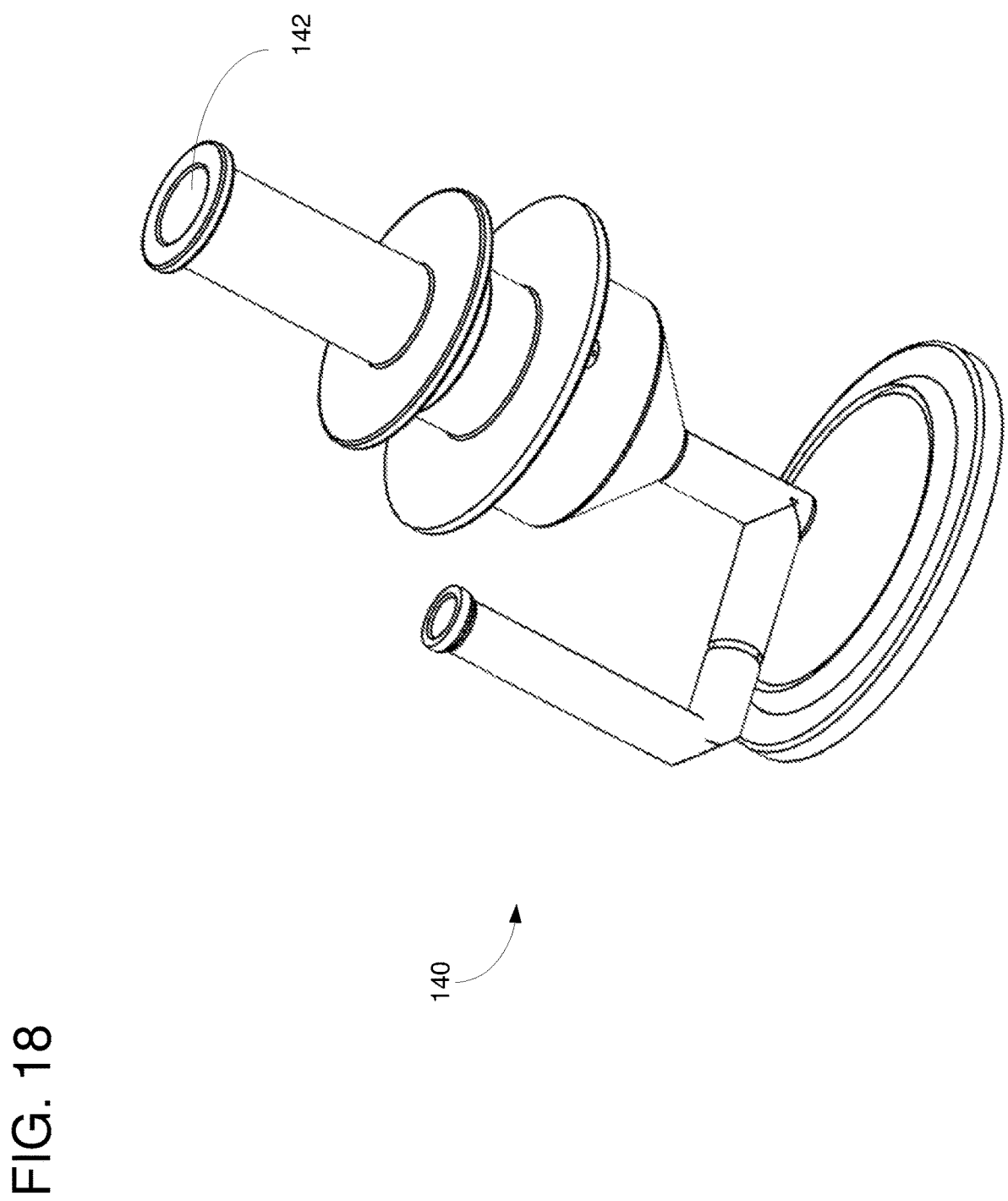
FIG. 18 shows an exemplary conduit assembly of the system of FIG. 1.
Figure 19:
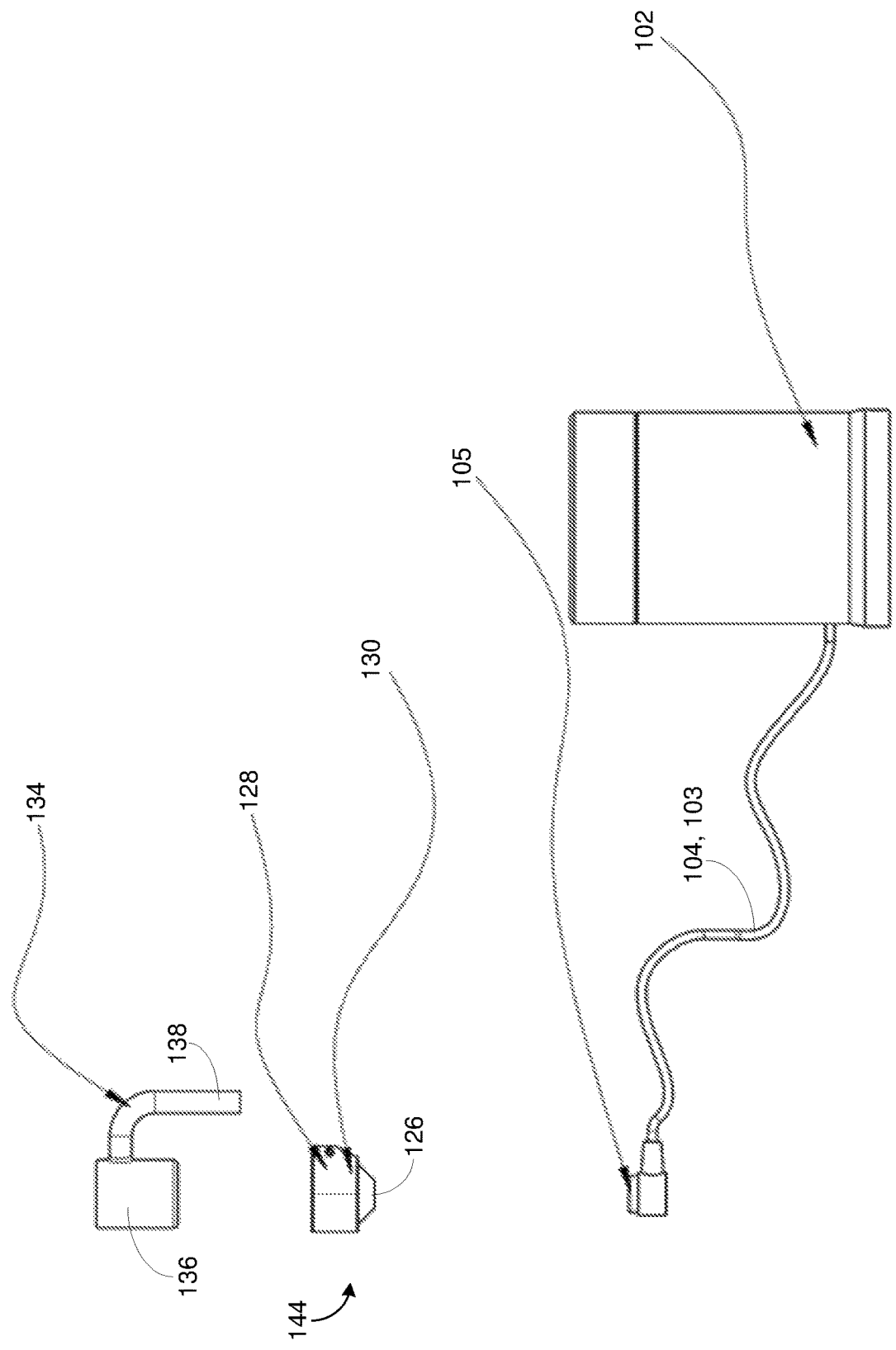
FIG. 19 shows an exploded view of the container, heating assembly, power cord, and battery of FIG. 1.

A container member 134, shown in FIG. 17, can comprise a therapeutic agent container portion 136 and a tube or conduit portion 138 in fluid communication with the container portion 136. The container portion 136 can have a cylindrical shape including an inner bore 164 in which liquid therapeutic agent can be received. In some embodiments, one or more portions of the container member 134 can comprise quartz or other heat-resistant materials. As shown in FIG. 20, the therapeutic agent container portion 136 can be placed in the holder 128 with a lower wall 137 placed against the heating element 130. Thus, as the heating element 130 increases in temperature, the container member 134 also increases in temperature. Once the container member 134 reaches a desired temperature, a user can place a therapeutic agent to be vaporized into the therapeutic agent container portion 136. When the container member 134 is at a sufficient temperature, placing liquid agent inside the container causes the agent to vaporize. A cap can then be placed over the therapeutic agent container portion 136 such that the vapor travels through the tube 138 and into the conduit assembly 140 coupled to tube 138, as shown in FIG. 1. A reservoir 141 of the conduit assembly 140 can be filled with water, if desired, and the vapor can pass through the conduit assembly and exit through an opening 142 where it can be inhaled by a user. FIG. 18 illustrates the conduit assembly 140 without the reservoir.

In operation, referring to FIG. 20, the battery 102 outputs a variable voltage/current through the power cable 104. The metallic connector 105 at the end of the power cable 104 can be coupled to the magnetic connector 124, which is housed within the magnet holder 126. The voltage/current output by the battery 102 creates a voltage/current at the metallic connector 105 and the magnetic connector 124 when the connectors 105, 124 are coupled together. The housing 128 can be positioned above the connector 124. In other embodiments, the connector 124 can extend at least partially into the housing 128. The washer 132 can be placed within the housing 128 and the ceramic plate 131 of the heating element 130 can be placed on top of the washer. The output pins 125a, 125b (FIG. 12) of the connector 124 can extend through the openings 129a, 129b (FIG. 14) in the housing 128 and through the openings 135a, 135b (FIG. 16) in the washer 132 and can be connected to the input pins 133a, 133b (FIG. 15) of the heating element 130. The connection between the output pins 125a, 125b and the input pins 133a, 133b ensures that the voltage/current output by the battery 102 is transferred to the heating element 130 to cause the heating element to increase in temperature. The washer 132 beneath the ceramic plate 131 can thermally isolate or prevent the magnetic connector 124 from excessive heating, avoiding loss of magnetic connectivity with the metallic connector 105 of the power cable 104.

Still referring to FIG. 20, the container portion 136 of the container member 134 can be placed on top of the heating element 130. As the heating element 130 increases in temperature, because the container member 134 is in contact with the heating element, the container member increases in temperature as well. When the container member 134 reaches a desired temperature, which can be controlled by varying the voltage/current output by the battery 102, liquid therapeutic agent can be placed in the container portion 136 of the member 134 and the container portion can be covered. The liquid agent will vaporize, and the vapor can travel through the tube 138 into the conduit assembly 140, as shown in FIG. 1. The vapor can then exit the opening 142 in the conduit assembly 140 and it can be inhaled by a user.

Figure 22:
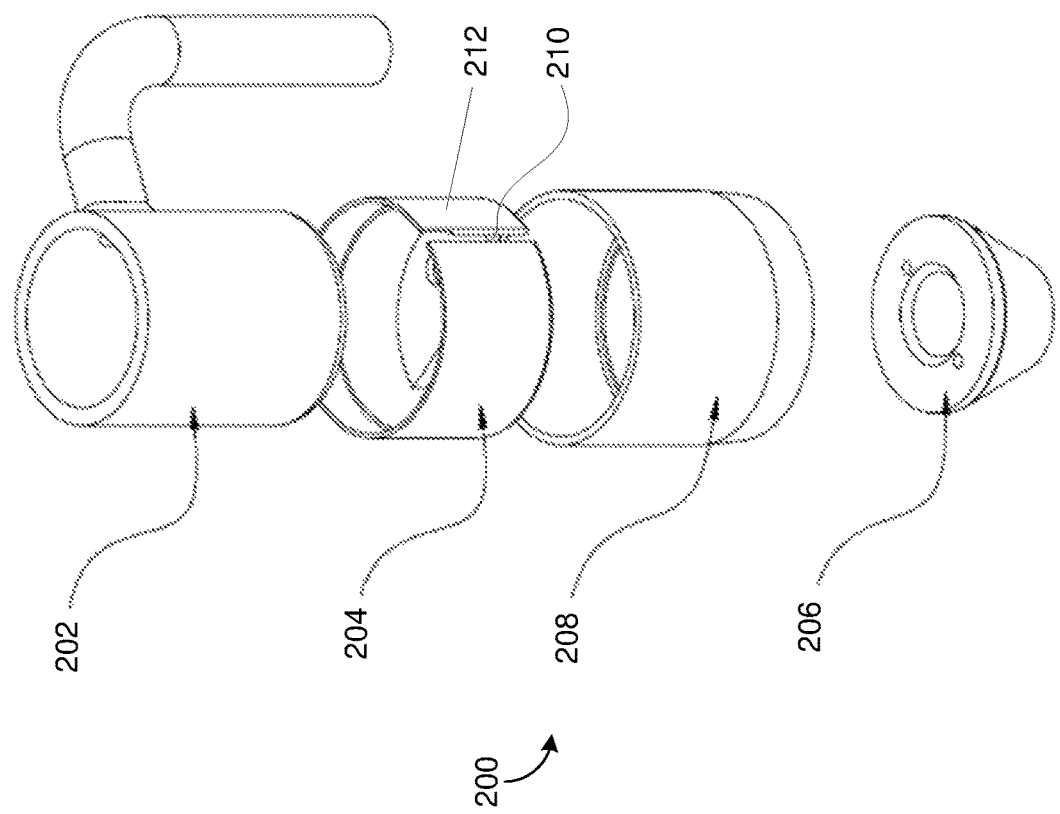
FIG. 22 shows an exploded perspective view of an exemplary heating assembly, according to another embodiment.

FIG. 22 illustrates another embodiment of a heating assembly 200. Heating assembly 200 can generally include a container member 202, a heating element clamp 204, a magnetic connection clamp 206, and an outer housing or sleeve 208. The components of heating element assembly 200 can advantageously be coupled together without the use of fasteners such as screws.

A heating element (such as heating element 130 described previously) can be disposed within the heating element clamp 204. Similar to housing 128, the heating element clamp 204 can comprise an opening or channel 210 extending through a thickness of the outer wall 212. The inner diameter of the heating element clamp 204 can be reduced by compressing/squeezing/deforming the outer wall 212 such that the width of the channel 210 is narrowed. A portion of the container member 202 (e.g., a lower portion) and a portion of the magnetic connection clamp 206, can each be disposed within the heating element clamp 204 such that the heating element is disposed between them. Thus arranged, the outer sleeve 208 can be slid over the components 202, 204, 206 to secure them in place relative to one another by compressing the outer wall 212 to reduce the inner diameter of the heating element clamp 204.

Explanation of Terms

For purposes of this description, certain aspects, advantages, and novel features of the embodiments of this disclosure are described herein. The disclosed exemplary methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation. All features described herein are independent of one another and, except where structurally impossible, can be used in combination with any other feature described herein.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language. As used in this application, directional terms such as "upper" or "lower" can be rotated and considered to be in different orientations.

In some examples, values, procedures, or apparatus may be referred to as "lowest," "best," "minimum," or the like. Such descriptions are intended to indicate that a selection among many alternatives can be made, and such selections need not be better, smaller, or otherwise preferable to other selections.

In the description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

Unless otherwise indicated, all numbers expressing material quantities, angles, pressures, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under test conditions/methods familiar to those of ordinary skill in the art. When directly and explicitly distinguishing embodiments from discussed prior art, the embodiment numbers are not approximates unless the word "about" is recited. Furthermore, not all alternatives recited herein are equivalents.

In view of the many possible embodiments to which the principles of the disclosure may be applied, it should be recognized that the illustrated embodiments are only preferred examples and should not be taken as limiting the scope of the disclosure. Rather, the scope of the disclosure is at least as broad as the following claims. I therefore claim all that comes within the scope of these claims.

The invention claimed is:

1. A heating element assembly for a vaporizing apparatus, comprising:
    a housing comprising an outer wall defining an inner bore and a base portion disposed within the inner bore, the base portion defining an upper well portion and a lower well portion, the upper well portion configured to receive at least a portion of a therapeutic agent container;
    a heating element disposed within the housing and configured to increase in temperature when a current is applied to the heating element;
    a magnetic connector disposed adjacent the housing and configured to be coupled to the heating element; and
    a spacing member disposed between the heating element and the magnetic connector;
    wherein the magnetic connector is configured to be coupled to an electric power source.

2. The assembly of claim 1, wherein the housing comprises a channel extending through a thickness of the outer wall such that an inner diameter of the housing is variable to clamp the therapeutic agent container, heating element, magnetic connector, and spacing member together.

3. The assembly of claim 2, further comprising a fastener extending across a width of the channel, the fastener configured to retain the housing in a clamped configuration.

4. The assembly of claim 2, further comprising an outer sleeve configured slide over the housing to reduce the inner diameter of the housing.

5. The assembly of claim 1, wherein the magnetic connector is disposed at least partially within a magnet holder coupled to the housing.

6. The assembly of claim 5, wherein the lower well portion is configured to receive at least a portion of the magnet holder.

7. The assembly of claim 1, wherein the spacing member comprises a silicone washer.

8. The assembly of claim 1, wherein the base portion of the housing comprises at least a first opening and the spacing member comprises at least a second opening axially aligned with the first opening.

9. The assembly of claim 8, wherein the heating element comprises a circular disc and at least one input pin extending from the disc through the first opening of the housing and the second opening of the spacing member.

10. The assembly of claim 9, wherein the magnetic connector comprises a main body and at least one output pin extending from the main body through the first opening and the second opening.

11. A system comprising:
    a power source configured to output an adjustable current through a cable connected to the power source;
    a heating assembly couplable to the power source by the cable;
    a container member coupled to the heating assembly and configured to receive therapeutic agent-containing liquid; and
    a conduit assembly coupled to and in fluid communication with the container member;
    wherein the heating assembly comprises a magnetic connector magnetically couplable to the cable and a heating element disposed adjacent the container member and coupled to the magnetic connector; and
    wherein the heating assembly further comprises a housing in which the heating element, a portion of the magnetic connector, and a portion of the container member are disposed, the housing having a diameter variable between a first diameter and a second diameter, the second diameter configured to secure the magnetic connector and the container member against movement relative to the housing.

12. The system of claim 11, wherein the power source is a rechargeable battery.

13. The system of claim 11, wherein one end of the cable has a metallic surface configured to magnetically couple to the magnetic connector.

14. The system of claim 11, further comprising an outer sleeve configured slide over the housing to move the housing from the first diameter to the second diameter.

15. The system of claim 11, wherein the housing comprises an outer wall having a channel extending through a thickness of the outer wall, and wherein the housing can be secured at the second diameter by a fastener extending across a width of the channel.

16. The system of claim 11, wherein the heating assembly further comprises a silicone washer positioned between the heating element and the magnetic connector.

17. The system of claim 11, wherein the container member is configured to be heated by the heating element.

18. A vaporizer including the system of claim 11.

* * * * *